(12) United States Patent
Fine

(10) Patent No.: US 11,719,700 B2
(45) Date of Patent: *Aug. 8, 2023

(54) UPCONVERSION FOR MICROSCOPY

(71) Applicant: Alentic Microscience Inc., Halifax (CA)

(72) Inventor: Alan Marc Fine, Prospect (CA)

(73) Assignee: Alentic Microscience Inc., Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/349,682

(22) Filed: Jun. 16, 2021

(65) Prior Publication Data

US 2021/0311037 A1    Oct. 7, 2021

Related U.S. Application Data

(60) Continuation-in-part of application No. 16/868,270, filed on May 6, 2020, now Pat. No. 11,099,181, and
(Continued)

(51) Int. Cl.
*G01N 33/58* (2006.01)
*G01N 33/50* (2006.01)
(Continued)

(52) U.S. Cl.
CPC ........... *G01N 33/585* (2013.01); *G01N 21/77* (2013.01); *G01N 33/5094* (2013.01);
(Continued)

(58) Field of Classification Search
CPC ......... G01N 33/5094; G01N 33/54366; G01N 33/56983; G01N 33/587; G01N 33/588; G01N 33/585
See application file for complete search history.

(56) References Cited

U.S. PATENT DOCUMENTS 9,041,790 B2    5/2015  Fine et al.
9,075,225 B2    7/2015  Fine et al.
(Continued)

FOREIGN PATENT DOCUMENTS

TW    I641371    11/2018
TW    I642780    12/2018
(Continued)

OTHER PUBLICATIONS

PCT International Search Report and Written Opinion in International Appln. No. PCT/CA2021/050466, dated Jul. 27, 2021, 10 pages.
(Continued)

*Primary Examiner* — Gailene Gabel
(74) *Attorney, Agent, or Firm* — Fish & Richardson P.C.

(57) ABSTRACT

Two or more upconverting particles are attached to each unit of one or more units of a chemical component in a sample, to form, for each unit of the chemical component, a multi-particle complex including the unit of the chemical component and two or more corresponding upconverting particles. The sample is illuminated by input light having a first wavelength. Light is received at an imaging sensor, the received light including output light generated by at least a portion of the upconverting particles attached to the units of the chemical component, the output light having a second wavelength that is shorter than the first wavelength. One or more images of the sample are captured from the received light. Based on the captured one or more images, a presence or a level of the chemical component in the sample is determined.

20 Claims, 6 Drawing Sheets

Related U.S. Application Data a continuation-in-part of application No. 16/845,458, filed on Apr. 10, 2020, now Pat. No. 11,255,850, said application No. 16/868,270 is a division of application No. 16/368,707, filed on Mar. 28, 2019, now Pat. No. 10,684,278, said application No. 16/845,458 is a continuation-in-part of application No. 16/368,707, filed on Mar. 28, 2019, now Pat. No. 10,684,278.

(51) Int. Cl.
*G01N 21/77* (2006.01)
*G01N 33/53* (2006.01)
*G01N 33/543* (2006.01)
*G01N 33/569* (2006.01)

(52) U.S. Cl.
CPC ....... *G01N 33/5302* (2013.01); *G01N 33/543* (2013.01); *G01N 33/54366* (2013.01); *G01N 33/56983* (2013.01); *G01N 33/587* (2013.01); *G01N 33/588* (2013.01)

(56) References Cited

U.S. PATENT DOCUMENTS

| | | | |
|---|---|---|---|
| 9,518,920 | B2 | 12/2016 | Fine et al. |
| 9,720,217 | B2 | 8/2017 | Fine et al. |
| 9,910,254 | B2 | 3/2018 | Fine et al. |
| 9,952,417 | B2 | 4/2018 | Fine |
| 9,989,750 | B2 | 6/2018 | Fine et al. |
| 10,107,997 | B2 | 10/2018 | Fine |
| 10,114,203 | B2 | 10/2018 | Fine et al. |
| 10,684,278 | B1 * | 6/2020 | Fine ................. G01N 33/5302 |
| 11,099,181 | B2 | 8/2021 | Fine |
| 11,255,850 | B2 | 2/2022 | Fine |
| 2006/0216696 | A1 | 9/2006 | Goguen |
| 2014/0152801 | A1 | 6/2014 | Fine et al. |
| 2016/0041200 | A1 | 2/2016 | Fine et al. |
| 2016/0187235 | A1 | 6/2016 | Fine et al. |
| 2017/0074870 | A1 * | 3/2017 | Kon ..................... B01F 33/30 |
| 2017/0293133 | A1 | 10/2017 | Fine et al. |
| 2018/0284416 | A1 | 10/2018 | Fine et al. |
| 2019/0054466 | A1 | 2/2019 | Gershtein |
| 2020/0309772 | A1 | 10/2020 | Fine et al. |
| 2020/0309777 | A1 * | 10/2020 | Fine ................. G01N 33/54313 |
| 2021/0311038 | A1 * | 10/2021 | Fine ................. G01N 33/582 |
| 2022/0082557 | A1 | 3/2022 | Fine |

FOREIGN PATENT DOCUMENTS

| | | |
|---|---|---|
| WO | WO 2000068692 | 11/2000 |
| WO | WO 2011102903 | 8/2011 |
| WO | WO2012061778 | 5/2012 |
| WO | WO 2020191480 | 10/2020 |
| WO | WO 2021203201 | 10/2021 |

OTHER PUBLICATIONS

U.S. Appl. No. 16/368,707, filed Mar. 28, 2019, Fine.
U.S. Appl. No. 16/868,270, filed May 6, 2020, Fine.
U.S. Appl. No. 16845,458, filed Apr. 10, 2020, Fine.
Appleblom et al., "Homogeneous TR-FRET High-Throughput Screening Assay for Calcium-Dependent Multimerization of Sorcin", www.sbsonline.org, Society for Biomolecular Sciences, 2007, 7 pages.
Barua et al., "Challenges associated with Penetration of Nanoparticles Across Cell and Tissue Barriers: A Review of Current Status and Future Prospects", Nano Today, Apr. 2014, 9(2):223-243.
Bidinosti et al., "Novel one step immunoassays to Quantify a-Synuclein: Applications for Biomarker Development and High-throughout Screening", Journal of Biological Chemistry 287(40):33691-33705, Sep. 28, 2012, 16 pages.
Chang et al., "Novel Diagnostic and Predictive Biomarkers in Pancreatic Adenocarcinoma", International Journal of Molecular Sciences, Mar. 2017, 14 pages.
Chavda et al., "A Bead Aggregation Assay for Detection of Low-Affinity Protein-Protein Interactions Reveals Interactions between N-Terminal Domains of Inositol 1,4,5-Trisphosphate Receptors", PLOS/One, Mar. 2013, 7 pages.
Hashizume et al., "Openings Between Defective Endothelial Cells Explain Tumor Vessel Leakiness", Am. J. Pathol., Apr. 2000, 156(4):1363-1380.
International Search Report and Written Opinion in International Application No. PCT/CA2020/050286, dated Jun. 5, 2020, 9 pages.
Kattke et al., "FRET-based Quantum Dot Immunoassay for Rapid and Sensitive Detection of Aspergillus amstelodami" Sensors 2011, 15 pages.
Medintz et al., "Self assembled nanoscale biosensors based on quantum dot FRET donors", Nature Materials, Oct. 2003, 10 pages.
Miller et al., "Significance of Circulating Tumor Cells Detected by the CellSearch System in Patients with Metastatic Breast Colorectal and Prostate Cancer", Journal of Oncology, Dec. 2009, 8 pages.
Shao et al., "Diagnostic Technologies for Circulating Tumour Cells and Exosomes", Bioscience Reports, Feb. 2016, 36(1):E00292.
Shi et al., "Nanoparticles based fluorescence energy transfer (FRET) for biosensing applications", Journal of Materials Chemistry B, Royal Society of Chemistry, 2015, 17 pages.
Tagit et al., "Fluorescence Sensing of Circulating Diagnostic Biomarkers Using Molecular Probes and Nanoparticles", ACS Sensors, pubs.acs.org/acssensors, Oct. 25, 2017, 16 pages.
Taiwanese Office Action in TW Appln. No. 109110649, dated Mar. 5, 2021, 19 pages with English translation.
Verma et al., "Covalent Immobilization of Doxorubicin in Glycine Functionalized Hydroxyapatite Nanoparticles for pH-Responsive Release", New Journal of Chemistry, 2018, Abstract Only.
Wikipedia.org [online], "Immunoassay", published on May 17, 2021, retrieved on Jun. 14, 2021, retrieved from URL<https://en.wikipedia.org/wiki/Immunoassay>, 7 pages.
Zeng et al., "Constructions of Silver Triangular Nanoplates-Quantum Dots Fret Systems", Scientific Reports, www.nature.com/scientificreports, May 20, 2016, 8 pages.
Zorko et al., "Cell Penetrating Peptides: Mechanism and Kinetics of Cargo Delivery", Adv. Drug Deliv. Rev. Mar. 2005, 57:529-545.
Extended European Search Report in European Appln. No. 20779367.0, dated Feb. 5, 2022, 11 pages.
PCT International Preliminary Report on Patentability in International Appln. No. PCT/CA2020/050286, dated Oct. 7, 2021, 6 pages.

* cited by examiner

UPCONVERSION FOR MICROSCOPY

CROSS-REFERENCE TO RELATED APPLICATIONS

This application is a continuation-in-part of, and claims priority to, U.S. patent application Ser. No. 16/868,270, filed May 6, 2020, which is a divisional of U.S. patent application Ser. No. 16/368,707, filed Mar. 28, 2019, now U.S. Pat. No. 10,684,278. This application is also a continuation-in-part of, and claims priority to, U.S. patent application Ser. No. 16/845,458, filed Apr. 10, 2020, which is a continuation-in-part of U.S. patent application Ser. No. 16/368,707, filed Mar. 28, 2019.

BACKGROUND

This description relates to upconversion for microscopy.

Useful information about a sample, for example, of whole blood of a patient for purposes of diagnosis, can be derived from not only a complete blood count (CBC) of blood cells of various in the blood sample and their hemoglobin content but also from a chemical analysis of other blood components such as in the acellular portion of blood (e.g., the plasma). Such other components can include molecules and ions of various kinds.

Traditionally, both a CBC and a chemical analysis of blood are performed in a lab on large expensive machines using tubes of venous blood obtained by phlebotomy. Hours or days may be required for the chemical analysis to be completed and the results returned.

U.S. Pat. No. 9,041,790 described use of upconversion with contact microscopy as follows (beginning at line 3 of column 17):

In some embodiments, a thin layer of adhesive material 617 coats the imaging integrated circuit 613. Coatings with molecules having specific affinities can be used to exclude or enrich particular cells or other specimens of interest. Such treatment could also be used, in conjunction with fluorophores 616, nanoparticles or micro beads, for binding assays. Non-selective adhesives will create an imaging "stick patch" that could be used, as an example, for forensic applications. In some embodiments, a thin layer of light-transmissive material 614 containing fluorophores, phosphors or up-converters coats the photosensitive surface. Such molecules are excited at one wavelength and emit at another. In some embodiments, fluorophores are excited with wavelengths outside the spectrally sensitive range of the imaging integrated circuit and emitting, including by frequency upconversion, within the circuit's spectral range, thereby extending the useful spectral range of the imaging integrated circuit, e.g. into the X-ray spectrum. In some embodiments, the device further comprises a system for detecting Raman scattering. In some embodiments, the device further comprises a system for detecting X-ray fluorescence.

SUMMARY

This disclosure describes methods. In one aspect, the present disclosure describes a chemical component analysis method. Two or more upconverting particles are attached to each unit of one or more units of a chemical component in a sample, to form, for each unit of the chemical component, a multi-particle complex including the unit of the chemical component and two or more corresponding upconverting particles. The sample is illuminated by input light having a first wavelength. Light is received at an imaging sensor, the received light including output light generated by at least a portion of the upconverting particles attached to the units of the chemical component, the output light having a second wavelength that is shorter than the first wavelength. One or more images of the sample are captured from the received light. Based on the captured one or more images, a presence or a level of the chemical component in the sample is determined.

Implementations of this and other methods may include any one or more of the following features.

In some implementations, determining the presence or the level of the chemical component in the sample includes identifying locations of the upconverting particles in the sample.

In some implementations, determining the presence or the level of the chemical component includes identifying multi-particle complexes in the sample based on a close proximity of the two or more upconverting particles of each multi-particle complex.

In some implementations, determining the presence or the level of the chemical component includes identifying multi-particle complexes in the sample based on a brightness of the multi-particle complexes.

In some implementations, the two or more upconverting particles of each multi-particle complex are attached to the unit of the chemical component at different locations of the unit of the chemical component.

In some implementations, illuminating the sample is performed at a first time, and receiving the light is performed at a second time, a difference between the first time and the second time being at least about 1 µs.

In some implementations, the difference between the first time and the second time is less than an excited state lifetime of the upconverting particles attached to the units of the chemical component.

In some implementations, there is no wavelength filter between the sample and the imaging sensor.

In some implementations, the input light includes infrared light, and the output light includes visible light.

In some implementations, the two or more upconverting particles of each multi-particle complex include a first type of upconverting particle having a first excitation wavelength band and a second type of upconverting particle having a second excitation wavelength band different from the first excitation wavelength band, the first wavelength is within the first excitation wavelength band and outside the second excitation wavelength band, and the output light having the second wavelength is generated by the first type of upconverting particle.

In some implementations, the method includes illuminating the sample by additional input light having a third wavelength, the third wavelength within the second excitation wavelength band and outside the first excitation wavelength band. The method includes receiving additional light at the imaging sensor, the received additional light including additional output light generated by the second type of upconverting particles, the additional output light having a fourth wavelength that is shorter than the third wavelength. The method includes capturing one or more additional images of the sample from the received additional light and, based on the captured one or more images and the captured one or more additional images, determining the presence or the level of the chemical component in the sample.

In some implementations, determining the presence or the level of the chemical component in the sample includes associating one or more upconverting particles of the first type within each multi-particle complex, as identified in the captured one or more images, with one or more upconverting particles of the second type within the multi-particle complex, as identified in the captured one or more additional images, based on a close proximity of the one or more upconverting particles of the first type to the one or more upconverting particles of the second type within each multi-particle complex.

In some implementations, the chemical component is a first chemical component and the sample includes one or more second units of a second chemical component. The method includes attaching two or more upconverting particles to each second unit of the one or more second units of the second chemical component to form, for each unit of the second chemical component, a second multi-particle complex including the second unit of the second chemical component and two or more corresponding upconverting particles, in which the two or more upconverting particles of each second multi-particle complex include the first type of upconverting particle, the second type of upconverting particle, or both the first type of upconverting particle and the second type of upconverting particle. A first ratio, defined as a ratio of a number of the first type of upconverting particle to a number of the second type of upconverting particle within each multi-particle complex including a unit of the first chemical component, is different from a second ratio, defined as a ratio of a number of the first type of upconverting particle to a number of the second type of upconverting particle within each second multi-particle complex.

In some implementations, the method includes, based on a difference between the first ratio and the second ratio, distinguishing between multi-particle complexes including a unit of the first chemical component and second multi-particle complexes based on the captured one or more images and the captured one or more additional images.

In some implementations, illuminating the sample by the additional input light having the third wavelength is performed after receiving the light including the output light at the imaging sensor.

In some implementations, the method includes, prior to illuminating the sample, placing the sample at a surface of the imaging sensor, the imaging sensor including an array of light-sensitive elements within a near-field distance of the sample.

In some implementations, placing the sample at the surface of the imaging sensor includes forming a monolayer of the sample at the surface.

In some implementations, forming the monolayer includes confining the sample between the surface of the imaging sensor and a second surface opposite the surface of the imaging sensor.

In some implementations, attaching the two or more upconverting particles to each unit of the one or more units of the chemical component includes binding an attachment unit to each unit of the one or more units of the chemical component, each of the attachment units also being bound to an upconverting particle.

In some implementations, the attachment unit includes an antibody.

In some implementations, the attachment unit includes a capsid protein or other antigen from a pathogen, and the units of the chemical component include antibodies to the pathogen.

The disclosure also describes apparatuses. For example, in one aspect, the present disclosure describes an apparatus including an imaging sensor, a light source, and one or more computing devices communicatively coupled to the imaging sensor and the light source, the one or more computing devices configured to perform operations. The operations include causing the light source to illuminate a sample with input light having a first wavelength, and receiving, from the imaging sensor, data representative of one or more images of the sample illuminated by the input light. The sample includes one or more units of a chemical component, each unit of the one or more units being attached to two or more upconverting particles, to form, for each unit of the one or more units of the chemical component, a multi-particle complex including the unit of the chemical component and two or more corresponding upconverting particles. The one or more images are based on output light generated by at least a portion of the upconverting particles attached to the units of the chemical component and received at the imaging sensor, the output light having a second wavelength that is shorter than the first wavelength. The operations also include, based on the data representative of the one or more images, determining a presence or a level of the chemical component in the sample.

Implementations of this and other apparatuses may include any one or more of at least the following features.

In some implementations, determining the presence or the level of the chemical component in the sample includes identifying locations of the upconverting particles in the sample.

In some implementations, the operations include identifying the multi-particle complexes in the sample based on a close proximity of the two or more upconverting particles of each multi-particle complex.

In some implementations, the operations include identifying multi-particle complexes in the sample based on a brightness of the multi-particle complexes.

In some implementations, the two or more upconverting particles of each multi-particle complex are attached to the unit of the chemical component at different locations of the unit of the chemical component.

In some implementations, causing the light source to illuminate the sample with the input light includes sending, to the light source, a first signal to cause the light source to illuminate the sample with the input light at a first time. The operations include sending, to the imaging sensor, a second signal to cause the imaging sensor to capture the one or more images at a second time, in which a difference between the first time and the second time is at least about 1 μs.

In some implementations, the difference between the first time and the second time is less than an excited state lifetime of the upconverting particles attached to the units of the chemical component.

In some implementations, there is no wavelength filter between the sample and the imaging sensor.

In some implementations, the input light includes infrared light, and the output light includes visible light.

In some implementations, the two or more upconverting particles of each multi-particle complex include a first type of upconverting particle having a first excitation wavelength band and a second type of upconverting particle having a second excitation wavelength band different from the first excitation wavelength band. The first wavelength is within the first excitation wavelength band and outside the second excitation wavelength band. The output light having the second wavelength is generated by the first type of upconverting particle.

In some implementations, the operations include receiving, from the imaging sensor, data representative of one or more additional images of the sample, the one or more additional images based on additional light received at the imaging sensor. The received additional light includes additional output light generated by the second type of upconverting particles in response to illumination by additional input light have a third wavelength. The third wavelength is within the second excitation wavelength band and outside the first excitation wavelength band. The additional output light has a fourth wavelength that is shorter than the third wavelength. The operations include, based on the data representative of the one or more images of the sample and the data representative of the one or more additional images, determining the presence or the level of the chemical component in the sample.

In some implementations, determining the presence or the level of the chemical component in the sample includes associating one or more upconverting particles of the first type within each multi-particle complex, as identified based on the data representative of the one or more images, with one or more upconverting particles of the second type within the multi-particle complex, as identified based on the data representative of the one or more additional images, based on a close proximity of the one or more upconverting particles of the first type to the one or more upconverting particles of the second type within each multi-particle complex.

In some implementations, the chemical component is a first chemical component. The sample includes a second chemical component, each second unit of one or more second units of the second chemical being attached to two or more upconverting particles to form, for each second unit of the second chemical component, a second multi-particle complex including the second unit of the second chemical component and the two or more upconverting particles. The two or more upconverting particles of each second multi-particle complex include the first type of upconverting particle, the second type of upconverting particle, or both the first type of upconverting particle and the second type of upconverting particle. A first ratio, defined as a ratio of a number of the first type of upconverting particle to a number of the second type of upconverting particle within each multi-particle complex including a unit of the first chemical component, is different from a second ratio, defined as a ratio of a number of the first type of upconverting particle to a number of the second type of upconverting particle within each second multi-particle complex.

In some implementations, the operations include, based on a difference between the first ratio and the second ratio, distinguishing between multi-particle complexes including a unit of the first chemical component and second multi-particle complexes including a unit of the second chemical component based on the data representative of the one or more images and the data representative of the one or more additional images.

In some implementations, the imaging sensor includes a surface configured to receive the sample, and an array of light-sensitive elements. The surface is within a near-field distance of the array of light-sensitive elements.

In some implementations, the imaging sensor includes a surface configured to receive the sample. The apparatus includes a second surface opposite the surface of the imaging sensor, and a mechanism configured to move the second surface. The operations include sending a signal to the mechanism to cause the second surface to move towards the surface of the imaging sensor to form a monolayer between the second surface and the surface of the imaging sensor.

In some implementations, each unit of the one or more units of the chemical component is bound to an attachment unit, the attachment unit being bound to an upconverting particle.

In some implementations, the attachment unit includes an antibody.

In some implementations, the attachment unit includes a capsid protein or other antigen from a pathogen, and the units of the chemical component include antibodies to the pathogen.

In another aspect, this disclosure describes another method. The method includes attaching one or more upconverting particles to each unit of one or more units of a chemical component in a sample. The method includes placing the sample within a near-field distance of an imaging sensor, the imaging sensor includes an array of light-sensitive elements within a near-field distance of the sample. The method includes illuminating the sample by input light having a first wavelength. The method includes receiving light at the imaging sensor, the received light including output light generated by at least a portion of the upconverting particles attached to the units of the chemical component, the output light having a second wavelength that is shorter than the first wavelength. The method includes capturing one or more images of the sample from the received light. The method includes, based on the captured one or more images, determining a presence or a level of the chemical component in the sample.

In another aspect, this disclosure describes another apparatus. The apparatus includes an imaging sensor including a surface configured to receive a sample, and an array of light-sensitive elements within a near-field distance of the surface. The apparatus includes a light source and one or more computing devices communicatively coupled to the imaging sensor and the light source, the one or more computing devices configured to perform operations. The operations include causing the light source to illuminate the sample with input light having a first wavelength. The operations include receiving, from the imaging sensor, data representative of one or more images of the sample situated on the surface and illuminated by the input light having the first wavelength. The sample includes one or more units of a chemical component, each unit of the one or more units being attached to two or more upconverting particles, to form, for each unit of the one or more units of the chemical component, a multi-particle complex including the unit of the chemical component and two or more corresponding upconverting particles. The one or more images are based on output light generated by at least a portion of the upconverting particles attached to the units of the chemical component and received at the imaging sensor, the output light having a second wavelength that is shorter than the first wavelength. The operations include, based on the data representative of the one or more images, determining a presence or a level of the chemical component in the sample.

These and other aspects, features, implementations, and advantages (1) can be expressed as methods, apparatus, systems, components, program products, business methods, means or steps for performing functions, and in other ways, and (2) will become apparent from the following description and from the claims.

DETAILED DESCRIPTION

Figure 1:
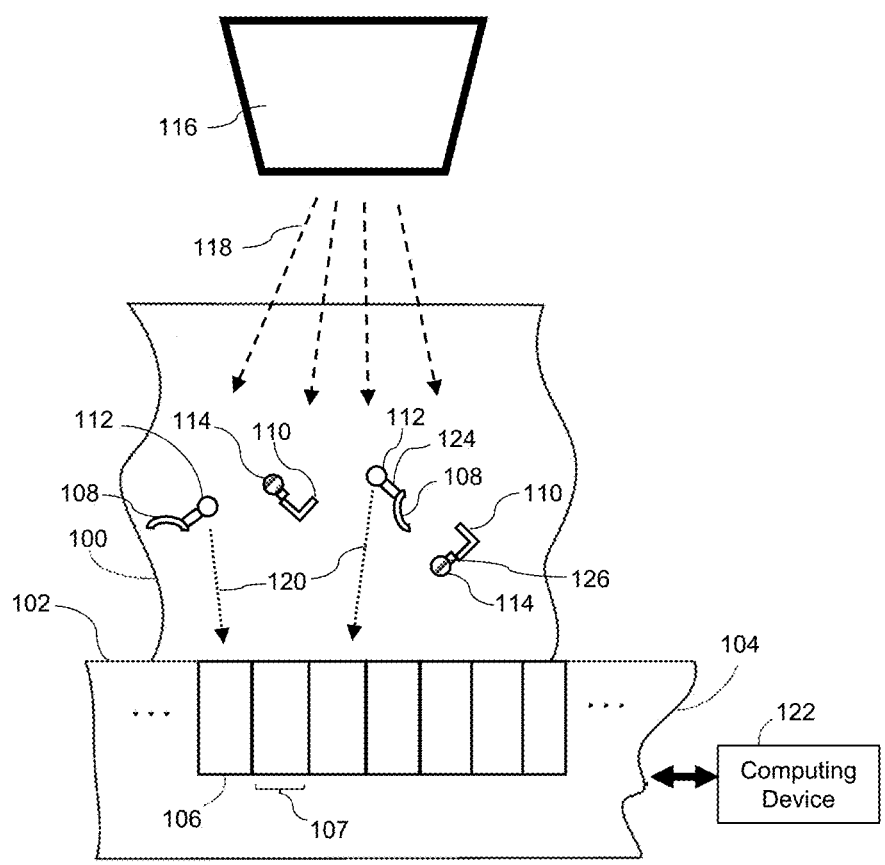
FIG. 1 is a schematic showing an example of upconverting particles in a sample.

This description relates to upconverting in microscopy. In particular, in certain implementations, this description relates to chemical assays using upconversion of particles.

Contact microscopy (sometimes referred to as near-field microscopy) can enable inexpensive, rapid chemical assays. In a contact microscopy procedure, a sample to be analyzed (e.g., a blood sample) is placed close to an imaging sensor that images the sample. The resulting images may be used directly to determine information about the sample, in some cases without requiring macroscopic lenses, sample flow, or sample focus adjustment. Additional information about contact microscopy can be found in U.S. Pat. Nos. 9,041,790, 9,075,225, 9,518,920, 9,952,417, 10,317,662, 10,502,666, and 10,684,278, United States patent application publications 2014/0152801 2019/0162648, and 2020/0309777, and U.S. patent application Ser. No. 17/193,680, all of which are incorporated here by reference.

In some cases, contact microscopy may include the use of indicators. These indicators, which may include fluorescing elements, directly-visible beads, or other visible units, can be attached to chemical units in a sample and imaged during contact microscopy. Differences between indicators can allow for multiplexed assays. Further details on indicators in contact microscopy can be found in United States patent application publications 2014/0152801 and 2020/0309777, and in U.S. Pat. No. 10,684,278.

In fluorescence microscopy, fluorescent units (e.g., fluorescent microspheres) are attached to chemical units in a sample. The sample is illuminated with input light having a first wavelength. The fluorescent units absorb the light and re-emit output light having a second wavelength, the second wavelength being, in most cases, higher than the first wavelength. An optical filter interposed between the sample and an imaging device filters out the light having the first wavelength, allowing only light from the fluorescent units to be transmitted. Because these fluorescent units can be attached (e.g., using particular antibodies) to particular chemical units in a sample, and because different types of fluorescent units can be used in a single sample, measurement of the detected output light can provide information about levels of multiple chemical components in the sample.

However, a simple combination of contact microscopy with fluorescence microscopy can present problems. Because the sample in contact microscopy is located very close to the imaging sensor (for example, within a near-field distance of the imaging sensor), in some cases a filter in between the two would require the sample to be placed farther away from the sensor than would be desirable, in some cases too far away to be useful. In order to maintain a near-field distance between the sample and the sensor, the filter would have to be very thin (e.g., less than a micron in thickness), a requirement that can be incompatible with effective filter operation.

Nor can optical filters necessarily, in some cases, be omitted from typical fluorescence microscopy devices. Because the wavelength of the output light in fluorescence microscopy is generally larger than the wavelength of the input light, most imaging sensors (e.g., silicon photodetectors) that detect the output light will also detect the input light. For example, if the lower-energy output light is able to trigger band-to-band transitions in the imaging sensor, the higher-energy input light is also generally able to trigger those transitions.

However, if the output light has a lower wavelength (higher energy) than the input light, then suitable configurations of the imaging sensor may allow for selective detection of only the output light without the need for a separate filter. For example, if particles in the sample absorb infrared light and emit visible light, then an imaging sensor that includes silicon photodetectors sensitive to visible light but not to infrared light will be more sensitive to the output light than to the input light.

Therefore, in some implementations, it may be beneficial to employ upconverting particles in microscopy applications. In contact microscopy applications, the use of upconverting particles can allow for fluorescent imaging while maintaining a near-field sample-to-sensor distance.

However, note that the methods and systems described herein need not be used in conjunction with contact microscopy, near-field imaging, or thin layers (e.g., monolayers) of sample. Rather, in some implementations the disclosed methods and systems may be used in conjunction with other microscopy methods such as, e.g., using macroscopic lenses or flow cytometry to image thick (many-layer) samples.

As shown in FIG. 1, in some implementations, a sample 100 is placed on a surface 102 of an imaging sensor 104. The imaging sensor 104 includes an array of light-sensitive elements 106 (e.g., photodetector pixels). The sample 100 is in contact with or within a near-field or quasi-near-field distance of the light-sensitive elements 106.

In this example, the sample 100 includes units 108 of a first chemical component and units 110 of a second chemical component. Units 108 of the first chemical component are attached to a first type of upconverting particle 112, and units 110 of the second chemical component are attached to a second type of upconverting particle 114.

Photon upconversion (or simply "upconversion") is a process in which lower-energy photons are converted into higher-energy photons. For example, two lower-energy photons may be converted into a higher-energy photon having an energy that is the sum of the energies of the two lower-energy photons. In some cases, energy is not conserved, and the higher-energy photon may have an energy that is less than the sum of the energies of the two lower-energy photons. Upconversion may occur through different physical mechanisms, including excited-state absorption, energy transfer upconversion, cooperative sensitization upconversion, and photon avalanche.

The upconverting particles 112, 114 may be upconverting nanoparticles. For example, the upconverting particles may have dimensions (e.g., diameters) of less than about 1 μm, less than about 500 nm, less than about 100 nm, or less than about 50 nm.

In various implementations, the upconverting particles 112, 114 may include one or more of quantum dots (e.g., graphene quantum dots), heterostructure upconverting nanoparticles, and rare earth-doped upconverting nanoparticles. For example, rare earth-doped upconverting nanoparticles may include a lattice (e.g., $NaYF_4$ or $LiYF_4$) doped with a lanthanide or an actinide (e.g., $Yb^{3+}$, $Er^{3+}$, $Tm^{3+}$, $Ho^{3+}$). The upconverting particles 112, 114 may upconvert wholly or partially plasmonically. A wide variety of materials may be used, in various concentrations, in order to configure the upconverting particles. For example, particular compositions of the upconverting particles 112, 114 may determine their excitation spectrum, their emission spectrum, or both.

This description uses the term "upconverting particles" broadly, to include, for example, upconverting units, compounds, and structures, which may have a wide variety of shapes and sizes.

In some implementations, the upconverting particles 112, 114 may be configured to undergo a sequential upconversion process. Rather than requiring the simultaneous absorption of two lower-energy photons (a requirement which may, in some implementations, decrease a quantum yield of upconversion), the upconverting particles 112, 114 may have intermediate excited states with relatively long lifetimes (e.g., from about 1 µs to about 1 ms), such that, under illumination, a reservoir of excited states exists and can be excited by further incoming photons to reach a higher-energy excited state. Recombination or relaxation from the higher-energy excited state causes the emission of a higher-energy output photon.

In some implementations, the upconverting particles 112, 114 may be small, e.g., to have a diameter of less than about 100 nm. In some implementations, the upconverting particles 112, 114 may have a diameter of less than about 50 nm. In some implementations, the upconverting particles 112, 114 may have a diameter of less than about 20 nm.

In some implementations, the upconverting particles 112, 114 may be doped with $Nd^{3+}$, which may provide an increased quantum efficiency for upconversion and allow for the upconverting particles to be smaller than if another dopant were used (for the same quantum efficiency).

In some implementations, the upconverting particles 112, 114 may include a shell of $LiY_4$. This passivating shell may reduce excitation energy quenching by surface defects and ligand and solvent vibrational modes.

In some implementations, the upconverting particles 112, 114 may have an excitation wavelength of about 800 nm. 800 nm light is absorbed relatively weakly by water compared to longer wavelengths of light (for example, 980 nm), and, therefore, the use of upconverting particles excited at about 800 nm may allow for a higher intensity of light to be absorbed by the upconverting particles.

In some implementations, the upconverting particles 112, 114 have an excitation wavelength outside a CMOS detection band. For example, the upconverting particles 112, 114 may have an excitation wavelength greater than 1000 nm, greater than 1250 nm, or greater than 1500 nm, such as about 1550 nm. The excitation wavelength may be less than 2000 nm. Having an excitation wavelength outside a CMOS detection band can allow upconverted light (which may fall inside the CMOS detection band) to be detected while reducing or excluding detection of the excitation light.

In some implementations, the upconverting particles 112 attached to the units 108 of the first chemical component have a different excitation spectrum from the upconverting particles 114 attached to the units 110 of the second chemical component. For example, the upconverting particles 112 may absorb light strongly in a first wavelength band, and the upconverting particles 114 may absorb light strongly in a second wavelength band, the first wavelength band being different from the second wavelength band. In some implementations, the first wavelength band may be non-overlapping with the second wavelength band. In some implementations, the first wavelength band may overlap the second wavelength band.

The sample 100 in the example of FIG. 1 is within a near-field distance of the array of light-sensitive elements 106. In various implementations, the near-field distance may include distances less than about $10\lambda$, distances less than about $5\lambda$, distances less than about $2\lambda$, distances less than about $\lambda$, or distances less than about $\lambda/2$, where $\lambda$ may be a wavelength of light to which the light-sensitive elements 106 are sensitive. In some implementations, $\lambda$ is a wavelength of light emitted by a light source used to illuminate the sample 100. In some implementations, $\lambda$ is a wavelength of upconverted light emitted by the upconverting particles (e.g., a peak wavelength of the upconversion emission spectrum). In some implementations, $\lambda$ may be a wavelength in the visible band of wavelengths (e.g., 500 nm or 600 nm).

In some implementations, the near-field distance may include distances less than about a width (e.g., width 107) of each light-sensitive element 106. In some implementations, the near-field distance may include distances less than about half a width of each light-sensitive element 106. In some implementations, each light-sensitive element 106 may have a width of about 5 µm or smaller. In some implementations, each light-sensitive element 106 may have a width of about 1 µm or smaller. In some implementations, each light-sensitive element 106 may have a width of about 500 nm or smaller. In some implementations, each light-sensitive element 106 may have a width of about 250 nm or smaller.

Because the sample 100 is within a near-field distance of the array of light-sensitive elements 106, the sample 100 may be imaged by the imaging sensor 104 at a resolution that surpasses the theoretical diffraction limit (Abbe limit or Rayleigh criterion) for microscopy, or at a resolution that is higher than if the sample 100 were at a non-near-field distance from the array of light-sensitive elements 106. Each light-sensitive element 106 collects light mostly from a portion of the sample that is within the near-field distance from the light-sensitive element 106, such that elements in the sample that are, for example, directly above a particular light-sensitive element will affect light absorbed by the particular light-sensitive element.

In some implementations, the surface of an imaging sensor may be within a near-field distance of the light-sensitive elements of the imaging sensor, such that a sample placed on the surface is within a near-field distance of the light-sensitive elements of the imaging sensor.

A light source 116 illuminates the sample 100 with input light 118. In the example of FIG. 1, the input light 118 is within the excitation band of the first type of upconverting particles 112 but outside an excitation band of the second type of upconverting particles 114. Therefore, upconverted output light 120 (having a higher energy than the input light 118) is generated by the first type of upconverting particles 112 but not by the second type of upconverting particles 114.

In some implementations, the second type of upconverting particles 114 absorbs the input light 118 and emits upconverted output light (in some implementations, the output light having a different wavelength spectrum from a wavelength spectrum of the upconverted output light 120 emitted by the first type of upconverting particles 112), and an upconversion efficiency of the second type of upconverting particles 114 may be less than an upconversion efficiency of the first type of upconverting particles 112 for the input light 118.

The imaging sensor 104 captures one or more images of the sample 100. In some implementations, the imaging sensor 104 may capture the one or more images in response to an instruction, e.g., an instruction sent by a computing device 122 communicatively coupled to the imaging sensor 104.

The one or more images may be based on light received at the light-sensitive elements 106. The received light may include one or both of the input light 118 (e.g., input light 118 that passes through the sample 100 or is scattered by elements in the sample 100) and the upconverted output light 120.

However, in some implementations, the light-sensitive elements 106 may be more sensitive to the upconverted output light 120 than to the input light 118. For example, the light-sensitive elements 106 may be silicon photosensors having a light sensitivity band between about 300 nm and about 1100 nm. If the input light 118 is infrared light (e.g., infrared light having a wavelength of about 1500 nm or about 1550 nm), and the output light 120 is visible light, then the one or more images may be formed substantially or entirely based on the output light 120 emitted by the first type of upconverting particle 112.

Therefore, the computing device 122 (or another computing device communicatively coupled to the imaging sensor 104 or the computing device 122) may analyze the one or more images to perform chemical analysis upon the sample 101. For example, the computing device 122 may determine a number of the first type of upconverting particles 112 in an imaged portion of the sample and determine a location in the sample corresponding to each imaged upconverting particle 112. The number of upconverting particles 112 and/or the determined locations of the upconverting particles 112 may be used to determine a presence or level (e.g., a concentration) or both of the first chemical component in the sample 100.

In some implementations, one or more images of the sample may be captured using a different wavelength of input light. For example, the light source 116 may be instructed by the computing device 122 to emit light (e.g., broadband light) in the visible spectrum, such that the imaging sensor 104 captures one or more images that include components in the sample (e.g., the units 108, 110 of the first and second chemical component). Locations of the upconverting particles 112, as determined using images captured under infrared input light, may be compared and correlated to locations of the units 108, 110 as determined using images captured under visible light. This correlation may be used to perform chemical analysis upon the sample 100, e.g., determine the presence or level or both of the first chemical component.

Because, in some implementations, multiple types of upconverting particles are attached, respectively, to units of multiple types of chemical component in the sample 100, the multiple types of upconverting particles may be separately imaged to separately perform chemical analyses directed to the multiple types of chemical components.

For example, after the one or more images are taken based on the output light 120 emitted in response to illumination by the input light 118, the light source 116 may emit other input light having a second wavelength that is, in some implementations, outside an excitation band of the first type of upconverting particles 112 but inside an excitation band of the second type of upconverting particles 114. The second type of upconverting particles 114 may absorb the other input light having the second wavelength and emit other upconverted output light, while the first type of upconverting particles 112 may not absorb the further input light, or may absorb the further input light less than the second type of upconverting particles 114 absorbs the further input light. Therefore, a second set of one or more images may be captured by the imaging sensor 104, the second set of one or more images based on the other upconverted output light emitted by the second type of upconverting particles 114. The second set of one or more images may be used to determine a presence or level or both of the second chemical component in the sample 100, as described above.

Although the example of FIG. 1 includes two types of chemical components and two types of upconverting particles, in some implementations there may be many types of upconverting particles, each type corresponding to a type of chemical component and having a different respective excitation band. The sample may be illuminated separately with light in each respective excitation band, and images may be captured separately to image each type of upconverting particle based on its respective upconverted output light. In some implementations, the upconverting particles may be designed to have narrow excitation bands, so that more types of upconverting particles can be separately imaged.

Although this description sometimes refers to input and output light having particular wavelengths, in some implementations input and output light may include light of multiple wavelengths, e.g., light having a spectrum centered at a particular central wavelength, or light having a spectrum in which a particular wavelength of light is most intense. In such implementations, references to particular wavelengths for input and output light may also refer to a central wavelength of a spectrum or a most intense wavelength in a spectrum.

In some implementations, the imaged sample includes whole blood drawn from a human or other animal. However, the sample analysis technology described in this description can also be applied to a wide range of contexts in which a sample (which may, but need not, be a biological sample) contains chemical components of interest (such as molecules or ions).

This description uses the term "sample" broadly to include, for example, any fluid or other mass or body of material that contains one or more analyzable chemical components and may or may not also contain one or more countable units of one or more types. The countable units may in some cases be opaque, translucent, or otherwise non-transparent to incident light. The analyzable chemical components may in some instances be transparent, translucent, or otherwise non-opaque to incident light. In some examples, the sample is whole blood containing countable blood cells of different types and also containing analyzable chemical components such as molecules or ions, to name two.

This description uses the term "chemical components" broadly to include, for example, chemical compounds, ions, molecules, and other constituents of a sample that may not be present in a form of discernible (e.g., visible) countable units.

This description uses the term "unit of a chemical component" broadly to include, for example, a single unit of a chemical component such as a single molecule, ion, or other constituent. In typical samples, there are many units of a given type of chemical component, for example, many molecules of a chemical compound. Units of a chemical component may be, but need not be, discrete, discernible, visible, identifiable, and subject to enumeration. In the case of whole blood, the units of a chemical component can include blood cells of different types.

This description uses the term "chemical analysis" broadly to include, for example, identification, enumeration, and quantification (e.g., determination of the level) of chemical components of one or more types in the sample. In some cases, chemical analysis can include identifying the presence of one or more molecules of one or more types and characterizing the amount, volume, or percentage of each of the types of molecules in the sample or in a particular volume of the sample.

As noted earlier, although the sample analysis technology has a broader range of applications, for convenience this description often discusses particular examples in which the sample includes whole blood or components of whole blood.

This description uses the term "whole blood" broadly to include, for example, blood in its original form drawn from a human or other animal. Whole blood includes countable units such as blood cells and blood plasma that includes chemical components. As described in the Wikipedia entry titled "Blood plasma," blood plasma is "a yellowish liquid component of blood that normally holds the blood cells in whole blood in suspension. In other words, it is the liquid part of the blood that carries cells and proteins . . . . It is mostly water (up to 95% by volume), and contains dissolved proteins (6-8%) (e.g. serum albumins, globulins, and fibrinogen), glucose, clotting factors, electrolytes (Na+, Ca2+, Mg2+, HCO3−, Cl−, etc.), hormones, carbon dioxide (plasma being the main medium for excretory product transportation) and oxygen." Clotting factors include molecules such as plasminogen and prothrombin that participate in clot formation.

This description uses the term "blood cells" broadly to include, for example, red blood cells (erythrocytes), white blood cells (leukocytes), rare blood cell types, ambiguous blood cell types, and platelets (thrombocytes).

Referring again to FIG. 1, the upconverting particles are attached to the units of the chemical component. This description uses the term "attached" broadly, to include both direct and indirect attachment. For example, two particles, units, or other elements may be attached directly (e.g., in contact and bound) to one another, or indirectly, (e.g., attached to one another by an attachment unit bound to each of the two particles, units, or other elements).

In some implementations, upconverting particles are attached to chemical units by an attachment unit that is bound to the upconverting particle and to the chemical unit. This description uses the term "attachment unit" broadly, to include, for example, antibodies (e.g., an antibody directed against a cluster-of-differentiation cell surface antigen, if the unit of the chemical component is a specific cell type), capsid proteins or other antigens from a pathogenic virus (e.g., if the unit of the chemical component is an antibody of the pathogenic virus, indicating prior exposure to the pathogenic virus), and other binding molecules and structures suitable for binding or attachment (e.g., direct attachment) to a unit of a chemical component.

In some implementations, the chemical component includes at least one of an antigen, a hormone, a biomarker, a drug, a viral capsid, a pathogen-directed antibody (for example, a virus-directed antibody), an oligonucleotide, or another molecule, cell, or particle.

For example, as shown in FIG. 1, a first type of attachment unit 124 is configured to bind to units 108 of the first chemical component and to the first type of upconverting particle 112. A second type of attachment unit 126 is configured to bind to units 110 of the second chemical component and to the second type of upconverting particle 114. In some implementations, attachment units are first bound to upconverting particles, and then the bound attachment unit-upconverting particle units are added to the sample for binding with units of chemical components.

Figure 2:
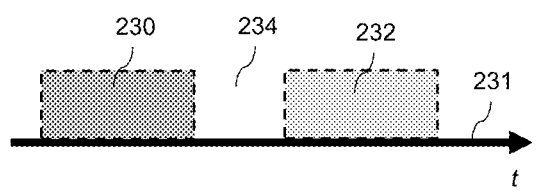
FIG. 2 is a timeline showing an example of processes performed by a microscopy apparatus.

Some implementations of the sample analysis technology may include time-gating. As shown schematically in FIG. 2 in reference to a time axis 231, a sample may be illuminated during a first time period 230, and images of the sample may be captured during a second time period 232, with a time gap 234 between the first and second time periods 230, 232. Because there is no active illumination during the second time period 232, any light incident on the imaging sensor during that time may be assumed to be upconverted light emitted by the upconverting particles. Time-gating may be used when light-sensitive elements of the imaging sensor are sensitive to both the input light and the upconverted output light, in order to increase a prominence of the desired upconverted output light in captured images. Time-gating may be combined with any of the contact microscopy implementations described in this description.

In some implementations, the time gap 234 is at least about 500 ns. In some implementations, the time gap 234 is at least about 1 µs. In some implementations, the time gap 234 is at least about 10 µs. In some implementations, the time gap 234 is less than an excited state lifetime of the upconverting particles.

Figure 3:
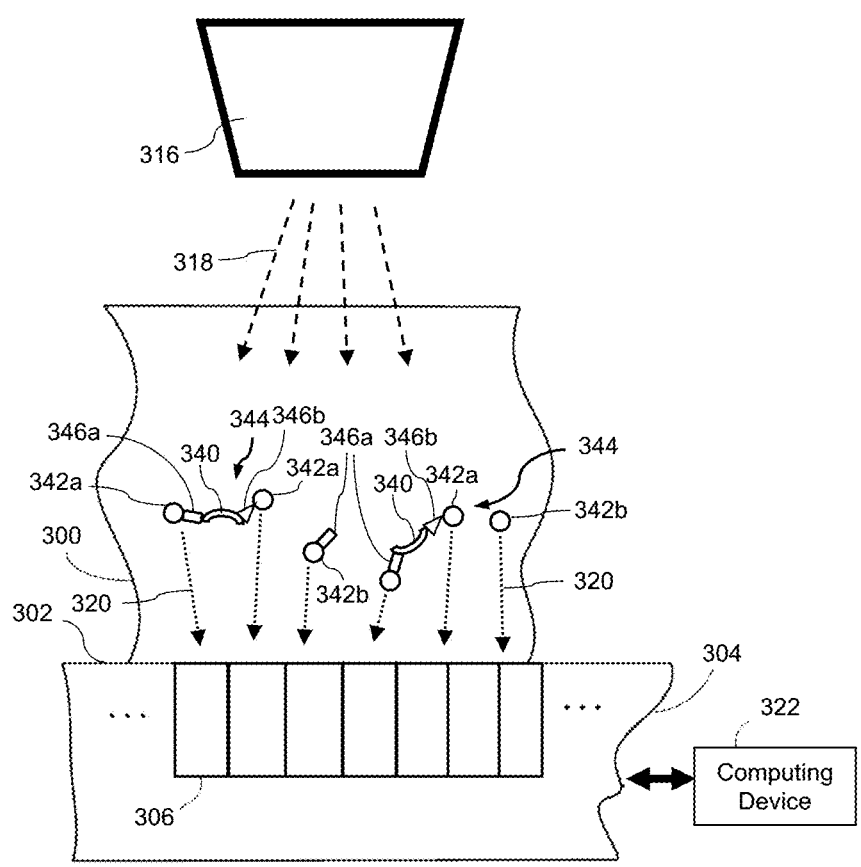
FIG. 3 is a schematic showing an example of upconverting particles in a sample.

In some implementations, upconverting particles form complexes with chemical components in a sample. In the example of FIG. 3, a sample 300 is placed on a surface 302 of an imaging sensor 304. The imaging sensor 304 includes an array of light-sensitive elements 306.

The sample 300 includes units 340 of a chemical component. Each unit 340 is attached to two upconverting particles 342a, to form, for each unit 340 of the chemical component, a multiple-particle complex 344 that includes two upconverting particles 342a and the unit 340 of the chemical component.

In the example of FIG. 3, the units 340 of the chemical component are attached to the upconverting particles 342a by attachment units 346a, 346b such that each multiple-particle complex 344 includes two upconverting particles 342a, two attachment units 346a, 346b, and the unit 340 of the chemical component. In some implementations, the attachment units 346a, 346b are different from one another, e.g., are configured to bind to different parts (e.g., epitopes) of the unit 340 of the chemical component.

In some implementations, not all upconverting particles present in the sample are attached to another element. For example, the sample 300 also includes one or more upconverting particles 342b that are not attached to a unit 340 of the chemical component.

As described above in reference to FIG. 1, a light source 316 illuminates the sample 300 with input light 318. The upconverting particles 342a, 342b upconvert the input light 318 and emit upconverted output light 320 that is received at the light-sensitive elements 306. For example, the input light 318 may be infrared light, and the output light 320 may be visible light. The input light 318 may be light to which the light-sensitive elements 306 are less responsive than to the output light 320.

Based on at least the output light 320, the imaging sensor 304 may capture one or more images of the sample 300. In some implementations, a time-gating process is employed, as described above.

The one or more images may be analyzed by the computing device 322 in order to carry out chemical analyses. For example, respective locations of the upconverting particles 342a, 342b may be determined, and upconverting particles 342a that are part of a multi-particle complex may be distinguished from upconverting particles 342b that are not part of a multi-particle complex. The upconverting particles may be distinguished based on, for example, a determined close proximity of the upconverting particles 342a of each multi-particle complex, compared to a proximity of each uncomplexed upconverting particle 342b to other upconverting particles. In some implementations, multi-particle complexes are identified based on the constancy of proximity of two or more particles of each multi-particle complex. The proximity may be measured in terms of absolute distance, or in terms of a proportion of a dimension of one or more of the particles, for example.

Proximity may alternatively or additionally be measured based on an intensity of luminescence. For example, a duplex complex including two upconverting particles may be on average twice as bright as a singleton upconverting particle, and a triplex complex including three upconverting particles may be on average three times as bright as a singleton upconverting particle. Different orders of complexed or uncomplexed beads can therefore be distinguished based on detected brightnesses in captured images. This method can be especially useful when individual upconverting particles cannot be distinguished in images, e.g., for subresolution imaging.

In some implementations, the computing device 322 may compare the captured one or more images to a second set of one or more images captured under visible illumination, and correlate locations of the upconverting particles 342a, 342b (as determined based on the captured one or more images) to locations of other elements in the sample (e.g., the units 340 of the chemical component) as determined based on the second set of one or more images.

Based at least on these determinations, chemical analyses may be carried out. For example, the computing device 322 may calculate a ratio of complexed upconverting particles 342a to uncomplexed upconverting particles 342b in the captured one or more images, look up a stored table or function that correlates such ratios to concentrations of the chemical component, and, based on the ratio, determine a concentration of the chemical component in the sample 300.

The use of upconverting particles may provide advantages over methods in which direct-imaging beads are used in contact microscopy processes. Direct-imaging beads are directly imaged based on light scattered by or passing through them, without separately emitting light. However, in some cases, direct-imaging beads must be a certain minimum size (e.g., >1 μm) in order to be distinguishable in images. This relatively high minimum size, compared to the nanoscale sizes of some implementations of the upconverting particles of this description, may limit a number of beads that may be attached to each unit of a chemical component, or may prevent the beads from being attached to very small units of a chemical component. By contrast, in some implementations, the upconverting particles are small enough to be attached to small units (e.g., for subcellular labeling) or to be attached to units in numbers of three, four or more. Because the upconverting particles emit upconverted light, the upconverting particles may be visible in captured images despite the small size of the upconverting particles in some implementations.

Figure 4A:
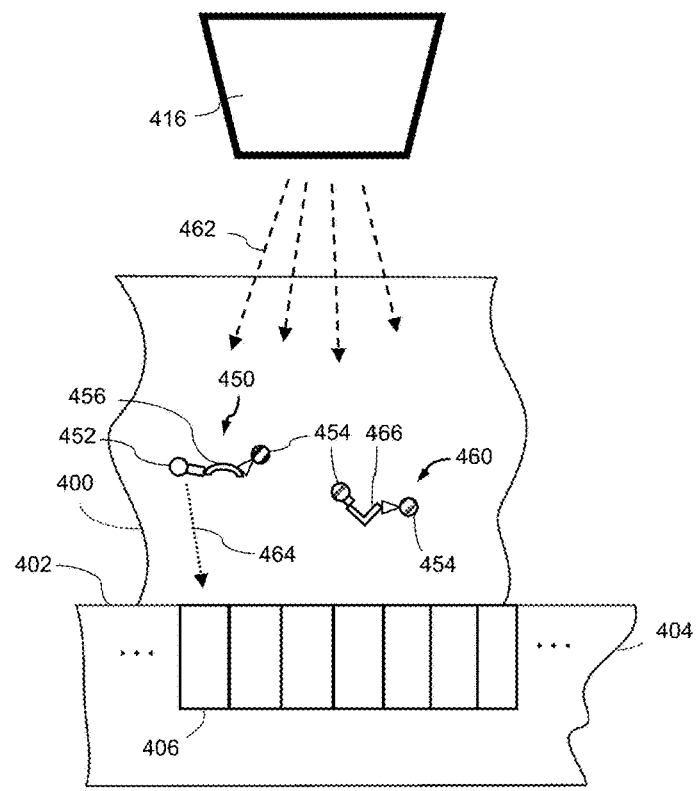
FIGS. 4A-4B are schematics showing illumination of a sample including upconverting particles by light of first and second wavelengths, respectively.
Figure 4B:
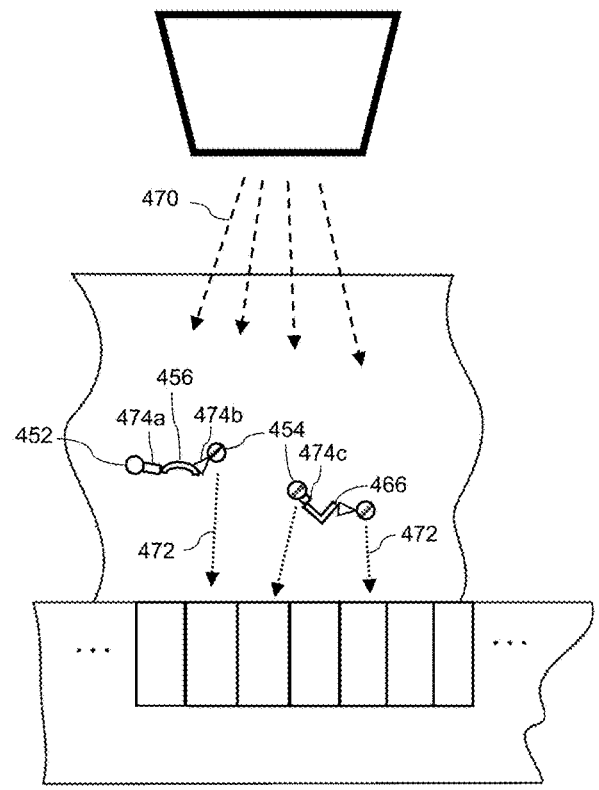

In some implementations, upconverting particles of a multi-particle complex may be different, and two or more types of chemical component may be in a sample. For example, in some implementations, as shown in FIGS. 4A-4B, a first multi-particle complex 450 includes a unit 456 of a first type of chemical component, a first type of upconverting particle 452, and a second type of upconverting particle 454. The first type of upconverting particle 452 may absorb light in a first range (e.g., at 1400 nm) and emit upconverted visible light, while the second type of upconverting particle 454 may absorb light in a second, different range (e.g., at 1500 nm) and emit upconverted visible light. In some implementations, the two absorption ranges are non-overlapping.

A second multi-particle complex 460 includes a unit 466 of a second type of chemical component and two upconverting particles 454 of the second type.

In the example implementation where the two types of upconverting particles 452, 454 absorb light at 1400 nm and 1500 nm, respectively, as shown in FIG. 4A, the sample 400 is first illuminated (by a light source 416) by 1400 nm input light 462, which the first type of upconverting particle 452 absorbs and uses to emit output light 464. The imaging sensor 404 (including photosensitive elements 406) captures a first set of one or more images that include the first type of upconverting particle 452 based on the output light 464.

Next, as shown in FIG. 4B, the sample is illuminated by 1500 nm input light 470, which the second type of upconverting particle 454 absorbs and uses to emit output light 472 (which may be the same as or different from the output light 464). The imaging sensor captures a second set of one or more images that include the second type of upconverting particle 454 based on the output light 472.

The first set and second set of images may be compared to identify the multi-particle complexes 450, 460 (e.g., based on determined proximities of the upconverting particles). Because the first multi-particle complex 450 includes one upconverting particle of each type, it may be determined that the first multi-particle complex 450 includes the unit 456 of the first chemical component. Because the second multi-particle complex 460 includes two upconverting particles 454 of the second type, it may be determined that the second multi-particle complex 460 includes the unit 466 of the second chemical component. These determinations may be based on an identification of a location (e.g., an absolute location with respect to the geometry of the imaging sensor) of each upconverting particle. Given these locations, upconverting particles satisfying a proximity criterion (e.g., within a particular distance of one another) can be associated as being part of a multi-particle complex.

Based on this information, chemical analyses may be carried out as described elsewhere in this description and in the documents incorporated by reference.

For example, a number of upconverting particles of a given type included in multi-particle complexes can be compared to upconverting particles of the same type that are not included in multi-particle complexes ("singleton" upconverting particles). By determining the proportion of complexed upconverting particles of the type to the total number of upconverting particles of the type (complexed and singleton, that is, uncomplexed) identified in the sample, it is possible to determine the level or amount or quantity or concentration of the target units (e.g., molecules) of the chemical component in the sample.

For example, a standard curve may be obtained, the standard curve providing a correspondence between i) the proportion of complexed upconverting particles of a first type to a total number of upconverting particles of the first type, and ii) a quantity or concentration of target units to which the upconverting particles of the first type are configured to attach to form multi-particle complexes.

The ratio (called the complex index) of counted complexed upconverting particles to the total number of counted upconverting particles (the total being the complexed or aggregated indicators and the singleton un-complexed indicators) is indicative of the level or amount or quantity or concentration of the units of the target chemical component in the sample. The count discriminates between, in various implementations, complexed or aggregated upconverting particles and singleton upconverting particles; complexes of multiple types of upconverting particle (e.g., based on different excitation and/or emitted wavelengths) and complexes of single types of upconverting particle; and/or complexes of multiple types of upconverting particle that include different respective combinations of types of upconverting particle. Taking into account the type of upconverting particle (and not just multi-particle presence) in analysis may be more accurate than assuming that all complexed upconverting particles are bound to units of the target chemical component and that all singleton upconverting particles are not bound to units of the chemical component. The results of the analysis can therefore take into account a) non-specific multi-particle complexes not bound to target chemical components (e.g., bound to one another) and b) target chemical components to which only singleton upconverting particles are bound. The latter effect may be relatively insignificant because very few target units are typically bound only to a singleton upconverting particle. The former effect can impede the ability of the sample analysis technology to detect a low level amount or quantity or concentration of the target chemical component.

Many or virtually all of the non-specific multi-particle complexes (multi-particle complexes that do not include a target chemical component) are formed during the process of coupling the attachment units to the upconverting particles and before the attachment units are bound to the units of the target chemical component, because more than one upconverting particle may bind to a single attachment unit. Therefore, complexes of two or more different types of upconverting particle identified in the imaged sample can be assumed to represent target units being assayed. The concentration of the upconverting particles in the sample can be low enough that the probability of two or more upconverting particles of different types landing in contact with each other absent a target unit may be very small, e.g., essentially zero. Therefore, by identifying, during image analysis, complexes including two or more different types of upconverting particle rather than simply multi-particle complexes of any type, false-positive target chemical component identifications can be reduced, improving (for example, by more than ten times) the sensitivity and consistency of the sample analysis technology.

In addition, the identification of different combinations of indicator types included in multi-indicator complexes can allow for highly multiplexed analysis, with multi-indicator complexes including three, four, or more indicators in various combinations being used to identify and analyze tens, hundreds, or thousands of different chemical components in a sample.

The complex index may be generalized to multiple types of upconverting particle and multiple types of multi-particle complexes. For example, rather than considering a ratio of complexed particles of a first type to a total number of particles of the first type, the performed analysis may determine a number of upconverting particles of two types included in multi-particle complexes that include upconverting particles of the two types, and compare that number to a total number of upconverting particles of the two types and/or to a number of singleton upconverting particles of the two types.

The wavelengths described in reference to FIG. 4 are examples; a wide range of input and output wavelengths may be used in accordance with this description.

Moreover, in some implementations, different types of upconverting particles differ in output wavelength instead of, or in addition to, differing in input wavelengths. For example, a first type of upconverting particle may emit light substantially in a first wavelength range, and a second type of upconverting particle may emit light substantially in a second, different wavelength range, which may, in some implementations, be non-overlapping with the first wavelength range. The different output wavelengths can be used to identify different types of upconverting particle in different multi-particle complexes and thereby identify multi-particle complexes that include particular types of chemical component. In some implementations, the different output wavelengths can be distinguished by the inclusion of filters between the sample and sensor elements.

Attachment units may be configured to bind to a specific type of chemical unit, a particular location on a chemical unit, or both. For example, in FIG. 4B, an attachment unit 474a may be configured to bind at a first location on a chemical unit 456, and an attachment unit 474b may be configured to bind at a second location on a chemical unit 456. An attachment unit 474c may be configured to bind at a particular location on chemical unit 466. For example, attachment units may bind at particular cell receptors on a chemical unit. Different types of upconverting particles can bind to units of chemical components using the same or different attachment units.

Various configurations of different attachment units bound to respective different upconverting particles may be used to form many permutations of upconverting particles in multi-particle complexes, allowing for multiplexed identification of many different chemical components within a single sample.

In this implementation, and in any implementation explained in this description, chemical units in the sample may be too small to directly image. The upconverting particles may act as labels that mark the small chemical units for detection and identification.

Figure 5:
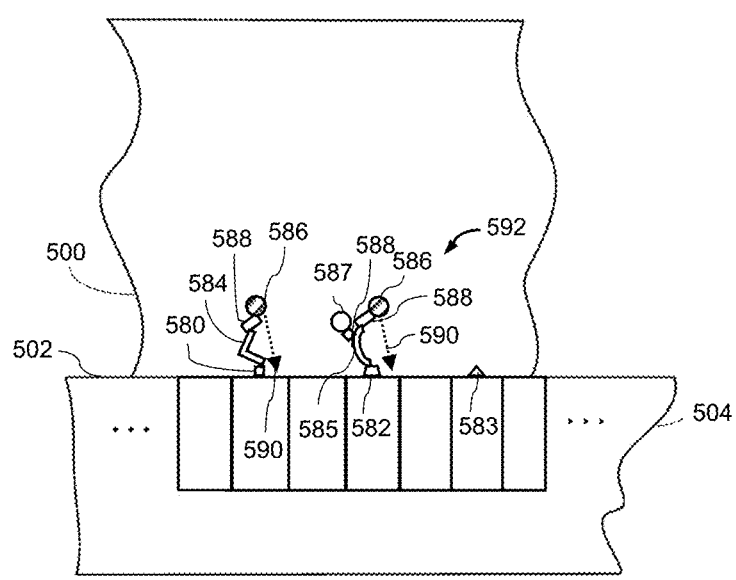
FIG. 5 is a schematic showing an example of upconverting particles attached to a surface.

In some implementations, units of one or more chemical components are attached at locations on a surface, and upconverting particles are attached to the units. In the example of FIG. 5, attachment units of a first type 580 and a second type 582 are bound (in some implementations, irreversibly bound) to particular locations of the surface 502 of an imaging sensor 504. The locations at which the attachment units are bound is known. For example, a storage or memory of a computing device may store data representing a correspondence between locations on the surface 502 and respective types of attachment units bound at those locations. In some implementations, the attachment units 580, 582 may be printed on the surface 502.

When a sample 500 is placed in contact with or within a near-field distance or quasi-near-field distance of the surface 502, chemical units of a first type 584 and chemical units of a second type 585 bind, respectively to the attachment units of the first type 580 and the attachment units of the second type 582. The attachment units 580, 582 may be configured to bind to the respective types of chemical units. The attachment units 580, 582 may be configured to bind at particular locations on the chemical units.

In addition, upconverting particles of one or more types (e.g., upconverting particles of a first type 586 and upconverting particles of a second type 587) attach to the chemical units 584, 585 via further attachment units 588. As described in reference to FIG. 4, the further attachment units 588 may be the same or different (e.g., configured to bind to different types of chemical component, or configured to bind to different types of upconverting particle). A multi-particle complex 592 is formed, the multi-particle complex 592 including one upconverting particle each of the first and second types 586, 587 and the second type of chemical unit 585.

The sample 500 is illuminated, and output light 590 upconverted by the first type of upconverting particle 586 is received at the imaging sensor 504, as described above. Based on one or more images captured by the imaging sensor 504, locations of the first type of upconverting particle 586 are determined. These locations can be cross-referenced with the known locations of the attachment units 580, 582 bound to the surface 502 to determine a type of attachment unit corresponding to each imaged upconverting particle 586, and, based on the type of attachment unit, the type of chemical unit 584 can be identified. Based on this information and, in some implementations, other information (e.g., a number of attachment units not detected as being attached to an upconverting particle), a level of a chemical component in the sample 500 can be determined (e.g., a level of the first type of chemical unit 584).

In some implementations, the sample 500 may be illuminated by further light that is outside an excitation band of the first type of upconverting particles 586 and within an excitation band of the second type of upconverting particle 587. Further output light upconverted by the second type of upconverting particle 587 may be received at the imaging sensor 504. As described above in reference to FIG. 4, a cross-reference between images based on the output light 590 and images based on the further output light may be used to identify multi-particle complexes, including the multi-particle complex 592, and to determine a level of the second type of chemical unit 585 in the sample. In some implementations, the determination may be based on a location at which the multi-particle complex 592 is bound at the surface 502.

Various permutations of types of upconverting particles included in each multi-particle complex and locations at which the multi-particle complexes are bound may be used to determine levels of many types on chemical components in a sample.

In the example of FIG. 5, no chemical units are bound to a third type of attachment unit 583, which may be configured to bind to a third type of chemical component. Therefore, no upconverting particles are located at those attachment units 582 (as determined based on the one or more captured images), and it may be determined that no, or few, units of the third type of chemical component are present in the sample 500.

In some implementations, the surface at which units of a chemical component are attached by attachment units is a different surface from the surface of the imaging sensor. For example, the surface may be a surface in contact with the sample and opposite the surface of the imaging sensor. The surface at which units of the chemical component are attached by attachment units may be a surface of a lid, cover, or other surface in contact with the sample and facing the imaging sensor, e.g., as described in one or more of U.S. Pat. Nos. 9,075,225, 9,518,920, and 10,317,662, United States patent application publication 2014/0152801, and U.S. patent application Ser. No. 17/193,680.

Attachment units may be bound to known locations of a surface in patterns, e.g., arrays. In some implementations, each bound attachment unit is attached directly above a corresponding light-sensitive element of an imaging sensor.

In some implementations, a monolayer of the sample is formed on the surface of an imaging sensor. The monolayer may be formed by a second surface that faces the surface of the imaging sensor and contacts the sample on an opposite side of the sample. The monolayer may have a thickness approximately matching a size of a unit of a chemical component in the sample, or another thickness. Examples of structures and techniques for forming such a monolayer are described in one or more of U.S. Pat. Nos. 9,075,225, 9,518,920, and 10,317,662, United States patent application publication 2014/0152801, and U.S. patent application Ser. No. 17/193,680.

This description uses the term "monolayer" broadly to include, for example, a volume of a sample that has a thickness no greater than the thickness of a particular type of unit in the sample, such as blood cells, so that across the monolayer two units cannot be stacked in the dimension defined by the thickness. In the case of a whole blood sample, the thickness of the monolayer could be in the range of about 1 micrometer to about 100 micrometers.

In some implementations, a second surface that acts to form a monolayer, as described above, may be the surface at which units of a chemical component are attached at known locations (or, equivalently, may be the surface at which attachment units, configured to bind to a particular chemical component, are bound at known locations).

In some implementations, because a monolayer of the sample is formed, light may be received at the imaging sensor without first interacting with units in the sample. For example, if the sample is a whole blood sample, some light (e.g., visible light emitted by a light source) may be received at the imaging sensor after passing through only blood plasma in the sample. In some implementations, plasma-based measurements may be combined with chemical analyses using upconverting particles.

In some implementations, because a monolayer of the sample is formed, an area-concentration of upconverting particles in images is decreased, and each upconverting particle or complex of upconverting particles can be individually distinguished, located, and identified.

Various features of FIGS. 1, 3, 4A-4B, and 5 may be simultaneously included in implementations. For example, the surface-binding implementations of FIG. 5 and the particle-complexing implementations of FIGS. 3 and 4A-4B may be simultaneously implemented in analyzing samples. In some implementations, some upconverting particles are included as part of multi-particle complexes, while other upconverting particles are singly attached to units of a chemical component.

Various choices of the units of the chemical component and attachment units may be used in a variety of applications, such as cytometry, in vitro diagnostics, environmental analysis, multiplex biochemical assays, serology, and gene expression, and combinations of them.

In an example of serology applied to a sample of blood from a patient, upconverting particles are bound to recombinant viral proteins of an infectious virus. The recombinant viral proteins bind to antibodies to the infectious virus within the sample. Complexes of two or more of the upconverting particles associated with an antibody of the infectious virus are identified or enumerated or both, and results of the identification or enumeration or both (potentially in concert with the identification or enumeration or both of single un-complexed upconverting particles) are used to determine a presence or level or both of the antibody of the infectious virus. Based on the determined presence or level or both of the antibody of the infectious virus, past exposure by the patient to the infectious virus can be identified. Samples besides blood may be used in addition to or instead of blood.

In the implementations explained in this description (e.g., the examples of FIGS. 1, 3, 4A-4B, and 5), because the sample is within a near-field distance of the array of light-sensitive elements, images of the sample (e.g., images showing upconverting particles) may be imaged with a higher resolution than if the sample were within a non-near-field distance of the light-sensitive elements. The difference may not be merely a difference of degree; rather, near-field optical effects may give rise to qualitatively different optical behavior that enables significantly improved imaging. In some implementations, because the sample is on a surface of an imaging sensor and within a near-field distance of the photosensitive elements, specific locations (either relative or absolute locations) of upconverting particles may be determined more accurately or more reliably than if the sample were imaged in a different way or using a different imaging apparatus.

Improvements in image resolution or upconverting particle identification and analysis may in turn improve results of chemical analyses applied to the sample. For example, the chemical analyses may be more accurate. In some implementations, the chemical analyses may be more sensitive (e.g., able to detect a lower concentration of a chemical component in the sample, compared to alternative methods).

The technologies explained in this description may enable more rapid sample analysis. For example, in some implementations, samples may be processed without requiring rinsing steps or flow. Therefore, a sample may be collected and immediately placed on the surface of the imaging sensor for processing. This may significantly speed up acquisition of test results (e.g., a blood count, or a result of an immunoassay) compared to alternative technologies.

In some implementations, upconverting particles may be configured for use in the contact microscopy technologies described here. For example, the upconverting particles may include surface features configured to bind to certain elements (e.g., to attachment units or to units of a chemical component). The upconverting particles may include shells or other coatings configured to stabilize the upconverting particles in the sample.

In some implementations, the upconverting particles may be configured to have particular excitation or emission characteristics. For example, a size (e.g., a diameter) of the upconverting particles may be tuned to adjust an excitation or emission band of the upconverting particles. In some implementations, concentrations of dopants (e.g., a lanthanide or an actinide) in the upconverting particles may be tuned to adjust an excitation or emission band of the upconverting particles.

Upconversion by the upconverting particles may take a variety of forms. The upconverting particles may upconvert from infrared light to visible light, from visible light to UV light, or from infrared light to UV light. In some implementations, the upconverting particles upconvert within a band of light wavelengths (e.g., from lower-energy visible light to higher-energy visible light).

In some implementations, the light source (e.g., light source 116 in FIG. 1) may include multiple separate light sources, each separate light source configured to emit light having a particular respective wavelength. Different separate light sources, illuminating at different wavelengths, may be used to selectively cause upconversion by different types of upconverting particles in the sample. In some implementations, the light source includes a tunable light source adjustable to emit light having a variety of wavelengths.

The light source may include, for example, a light-emitting diode or a laser (e.g., an infrared laser diode). The light source may emit in one or more of the infrared, visible, and ultraviolet ranges, and emitted light may be narrow-band or broad-band.

In some implementations, the light-sensitive elements are sensitive to a broad band of light. For example, silicon photosensors are broadly sensitive to light between about 300 nm and about 1100 nm. In some implementations, the light-sensitive elements are sensitive to a narrower range of light (e.g., sensitive to a particular color of visible light).

Although this description refers to a sample to be imaged as being disposed on a surface of an imaging sensor, in some implementations one or more layers or elements are interposed between the sample and underlying light-sensitive elements. Such layers may act to protect the sensors or to promote sample adhesion. For example, a hydrophilic layer may be on the surface of the imaging sensor. In some implementations, a thin, transparent support material of a disposable sample carrier may be between the sample and underlying light-sensitive elements.

Layers can also be optically active, possibly encompassing polarization filters, wavelength filters, microlenses, or combinations of these and other layer types. "Microlenses" here refers to small lenses that may, for example, transmit light to only one light-sensitive element, or may transmit light to only a relatively small number of light-sensitive elements (e.g., fewer than ten light-sensitive elements, fewer than 8 light-sensitive elements, fewer than five light-sensitive elements, or fewer than four light-sensitive elements), and which are within a near-field distance of the light-sensitive elements. Microlenses may be distinguished from "image-forming lenses," which refers at least to macroscopic lenses (e.g., lenses usable in the context of an optical bench) that transmit light representing a significant portion of a resulting image. In some implementations, there is no image-forming lens between the sample and the light-sensitive elements.

In some implementations, there is no optical wavelength filter between the sample and the light-sensitive elements. Therefore, the sample may be maintained within the near-field distance of the light-sensitive elements, and the upconversion methods described are usable to allow for selective imaging and detection of upconverting particles.

In some implementations, the sample is imaged while static, e.g., while not collectively flowing along a defined path. In some implementations the sample is imaged while flowing past the imaging sensor.

In some implementations, upconverting particles, attachment units, or both, are pre-deposited onto a portion of a contact microscopy apparatus. For example, in some implementations, upconverting particles bound to attachment units are dried on a surface (e.g., the surface of the imaging sensor or the second surface), and become attached to units of a chemical component when the sample is placed in contact with the surface.

In some implementations, the surface on which the upconverting particles (in some cases already bound to attachment units) are pre-deposited is disposable, e.g., the surface may be a surface of a disposable lid or cover, as described elsewhere in this disclosure. In some implementations, multiple varieties of disposable lid/cover may be available, each variety characterized by one or more types of upconverting particles and/or attachment units pre-deposited on the lid and suitable for analysis of one or more particular chemical components.

In some implementations, a sample is modified prior to placement on an imaging surface or while disposed on an imaging surface. For example, the sample may be diluted by addition of a chemical to the sample, or a viscosity of the sample may be increased by addition of a chemical to the sample. Examples of sample modification for contact microscopy can be found in U.S. Pat. Nos. 9,518,902 and 10,317,662 and United States patent application publication 2014/0152801.

Figure 6:
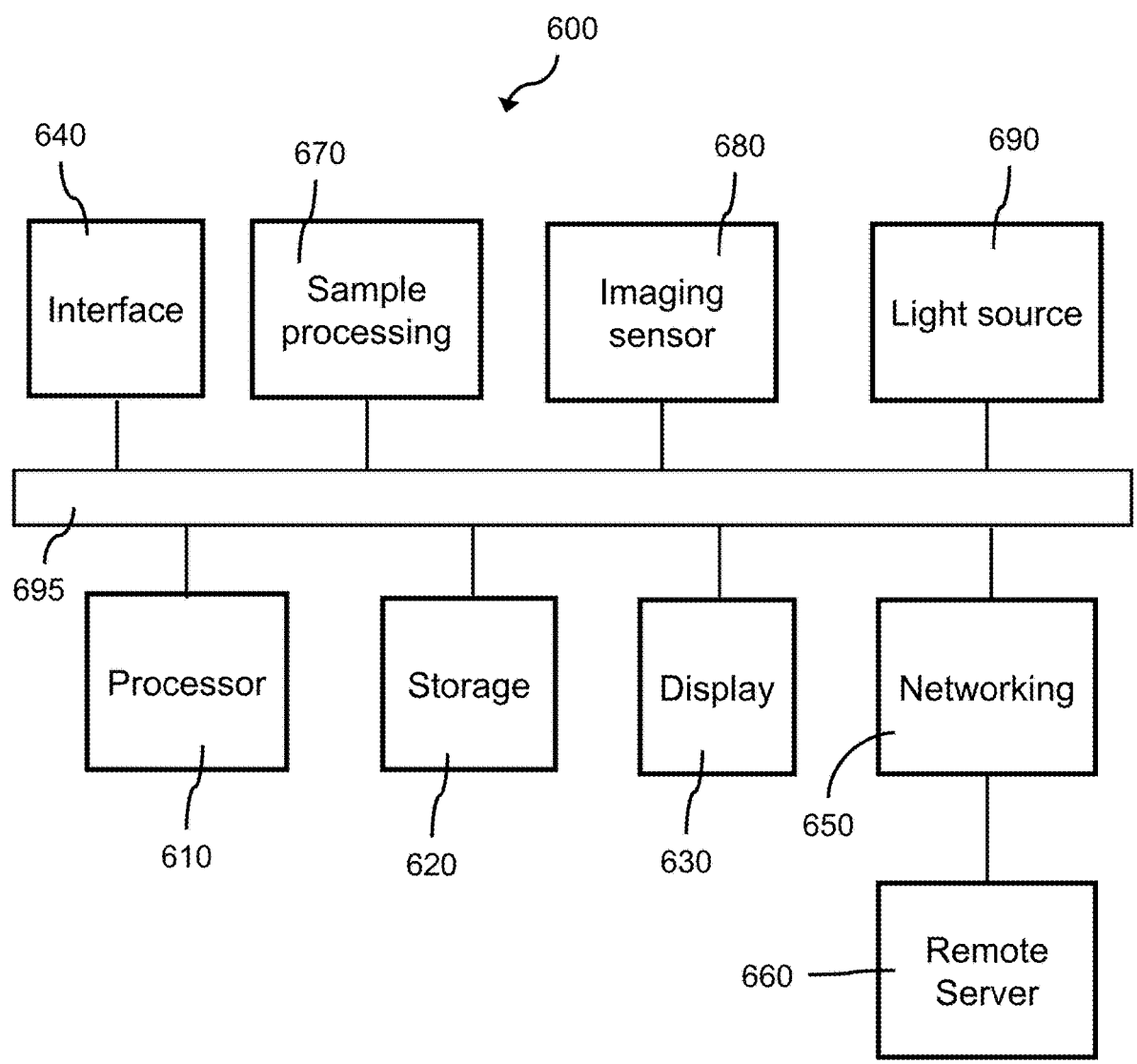
FIG. 6 is a block diagram showing an example microscopy system.

FIG. 6 shows an example system 600 according to some implementations. One or more processors 610 (which may be remotely located with respect to one another and which may perform different operations) may perform computational operations (e.g., image processing and analysis) and provide instructions to other elements of the system 600. A storage 620 may store captured images and other data usable by the processor 610. A display 630 and interface 640 (e.g., a touchscreen or keyboard) are usable by a user to control the system 600. A network module 650 may be used to transmit data, including captured images, to a remote server 660 (e.g., a cloud server). In some implementations, some or all processing functions (e.g., image analysis) may be performed by the remote server 660.

The one or more processors 610 may perform any of the image processing analysis steps described in this description, e.g., identifying locations of upconverting particles, identifying types of upconverting particles and types of multi-particle complexes, and determining levels of chemical components. Examples of analysis methods that may be used in contact microscopy can be found in U.S. Pat. Nos. 9,518,920 and 9,952,417, and in United States patent application publications 2014/0152801 and 2019/0162648.

Sample processing components 670 are configured to perform at least one or more of placing the sample in position on a surface of an imaging sensor, mixing the sample, and forming a monolayer of the sample. For example, the sample processing components may include mechanical components that control a second surface in contact with the sample, in order to mix the sample and form a monolayer of the sample. Details on contact microscopy apparatuses including these sample processing components can be found in U.S. Pat. Nos. 9,041,790, 9,075,225, 9,518, 920, 9,952,417, 10,317,662, and 10,502,666, and United States patent application publications 2014/0152801 and 2019/0162648.

An imaging sensor 680 and one or more light sources 690 are also included in the system, receiving instructions from the processor 610 or the interface 640. Interconnection components 695 transfer data between elements of the system 600.

In some implementations, a microscopy apparatus, as described in this description, may be portable. For example, some or all of the elements in system 600 may be implemented in a small, portable, relatively inexpensive sample analysis device.

A contact microscopy apparatus may also include, for example, features defining a sample space for the sample, alignment features, and structures serving to contain the sample and apparatus components, e.g., a body of a portable contact microscopy device. Details on contact microscopy apparatuses including these components can be found in U.S. Pat. Nos. 9,041,790, 9,075,225, 9,518,920, 9,952,417, 10,317,662, and 10,502,666, United States patent application publications 2014/0152801 and 2019/0162648, and U.S. patent application Ser. No. 17/193,680, all of which are incorporated here by reference.

A "near-field distance," as used in this disclosure, may be, for example, less than ten times a wavelength of light emitted by optical elements of the device, or less than five times a wavelength of light emitted by optical elements of the device, or less than two times a wavelength of light emitted by optical elements of the device, or less than a wavelength of light emitted by optical elements of the device. In some implementations, a near-field distance may be less than ten times a wavelength of light to which the imaging sensor is sensitive, or less than five times a wavelength of light to which the imaging sensor is sensitive, or less than two times a wavelength of light to which the imaging sensor is sensitive, or less than a wavelength of light to which the imaging sensor is sensitive. In some implementations, a near-field distance may be less than ten times a wavelength of light emitted by an upconverting particle, or less than five times a wavelength of light emitted by an upconverting particle, or less than two times a wavelength of light emitted by an upconverting particle, or less than a wavelength of light emitted by an upconverting particle.

All or part of the processes described herein and their various modifications (hereinafter referred to as "the processes"), including apparatus control functions (e.g., movement, illumination, and image capture instructions) and analysis functions (e.g., image analysis) can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers, e.g., as represented in FIG. 6. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit). Other embedded systems may be employed, such as NVidia® Jetson series or the like.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors or computer systems "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

Components may be coupled (e.g., communicably coupled) over one or more networks or physically within a device. Coupling may include the capability to transmit data, including instructions, back and forth between the components.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

In operation, the computer system may cause sample illumination by a light source and/or image capture by the image sensor by transmission and reception of appropriate signals. For example, the computer system may send one or more signals to a light source to cause the light source to illuminate the sample; may send one or more signals to a mechanism associated with a lid to cause the lid to move with respect to a sensor surface; may send one or more signals to an image sensor to cause the image sensor to capture one or more images of a sample; and may receive, from the image sensor, signals representative of images captured by the image sensor.

Various modifications will be readily apparent. For example, the actions described can, in some instances, be performed in a different order and still achieve desirable results. As one example, the processes depicted in the accompanying figures do not necessarily require the particular order shown, or sequential order, to achieve desirable results. In some cases, multitasking and parallel processing may be advantageous.

Accordingly, other implementations are also within the scope of the claims.

What is claimed is:

1. A method of determining a presence or a level of a chemical component in a sample comprising:
    attaching two or more upconverting particles to each unit of one or more units of a chemical component in a sample based on the two or more upconverting particles being configured to attach specifically to a corresponding unit of the chemical component, to form, for each unit of the one or more units of the chemical component, a multi-particle complex comprising the unit of the chemical component and two or more corresponding upconverting particles;
    illuminating the sample by input light having a first wavelength;
    receiving light at an imaging sensor, the received light including output light generated by at least a portion of the upconverting particles attached to the one or more units of the chemical component, the output light having a second wavelength that is shorter than the first wavelength;
    capturing one or more images of the sample from the received light including the output light generated by at least the portion of the upconverting particles;
    identifying one or more multi-particle complexes in the one or more images based on at least one of (i) a proximity of the two or more upconverting particles to one another in each of the one or more multi-particle complexes, or (ii) a brightness of the output light generated by the two or more upconverting particles; and
    based on identifying the one or more multi-particle complexes in the one or more images, determining a presence or a level of the chemical component in the sample.

2. The method of claim 1 in which determining the presence or the level of the chemical component in the sample comprises identifying locations of the upconverting particles attached to the one or more units of the chemical component.

3. The method of claim 1 in which the two or more upconverting particles of each multi-particle complex are attached to the unit of the chemical component at different locations of the unit of the chemical component.

4. The method of claim 1 in which illuminating the sample is performed at a first time, and in which receiving the light is performed at a second time, a difference between the first time and the second time being at least about 1 µs.

5. The method of claim 4 in which the difference between the first time and the second time is less than an excited state lifetime of the upconverting particles attached to the one or more units of the chemical component.

6. The method of claim 1 in which there is no wavelength filter between the sample and the imaging sensor.

7. The method of claim 1 in which the input light comprises infrared light, and in which the output light comprises visible light.

8. The method of claim 1 in which the two or more upconverting particles of each multi-particle complex include a first type of upconverting particle having a first excitation wavelength band and a second type of upconverting particle having a second excitation wavelength band different from the first excitation wavelength band,
   in which the first wavelength is within the first excitation wavelength band and outside the second excitation wavelength band, and
   in which the output light having the second wavelength is generated by the first type of upconverting particle.

9. The method of claim 8, in which the one or more images are one or more first images, and wherein the method comprises:
   illuminating the sample by additional input light having a third wavelength, the third wavelength within the second excitation wavelength band and outside the first excitation wavelength band;
   receiving additional light at the imaging sensor, the received additional light including additional output light generated by the second type of upconverting particles, the additional output light having a fourth wavelength that is shorter than the third wavelength;
   capturing one or more second images of the sample from the received additional light; and
   based on the captured one or more first images and the captured one or more second images, determining the presence or the level of the chemical component in the sample.

10. The method of claim 9, wherein determining the presence or the level of the chemical component in the sample comprises:
    associating one or more upconverting particles of the first type within each multi-particle complex, as identified in the one or more first images, with one or more upconverting particles of the second type within the multi-particle complex, as identified in the one or more second images, based on a proximity of the one or more upconverting particles of the first type to the one or more upconverting particles of the second type within each multi-particle complex, the proximity based on the one or more first images and the one or more second images.

11. The method of claim 9 in which the chemical component is a first chemical component and in which the sample comprises one or more additional units of a second chemical component, the method comprising:
    attaching two or more upconverting particles to each additional unit of the one or more additional units of the second chemical component to form, for each unit of the second chemical component, a second multi-particle complex including the additional unit of the second chemical component and two or more corresponding upconverting particles,
    in which the two or more upconverting particles of each second multi-particle complex include the first type of upconverting particle, the second type of upconverting particle, or both the first type of upconverting particle and the second type of upconverting particle, and
    in which a first ratio, defined as a ratio of a number of the first type of upconverting particle to a number of the second type of upconverting particle within each multi-particle complex including a unit of the first chemical component, is different from a second ratio, defined as a ratio of a number of the first type of upconverting particle to a number of the second type of upconverting particle within each second multi-particle complex.

12. The method of claim 11, comprising
    based on a difference between the first ratio and the second ratio, distinguishing between multi-particle complexes including a unit of the first chemical component and second multi-particle complexes based on the captured one or more first images and the captured one or more second images.

13. The method of claim 9 in which illuminating the sample by the additional input light having the third wavelength is performed after receiving the light including the output light at the imaging sensor.

14. The method of claim 1, comprising, prior to illuminating the sample, placing the sample at a surface of the imaging sensor, the imaging sensor comprising an array of light-sensitive elements within a near-field distance of the sample.

15. The method of claim 14 in which placing the sample at the surface of the imaging sensor comprises forming a monolayer of the sample at the surface.

16. The method of claim 15 in which forming the monolayer comprises confining the sample between the surface of the imaging sensor and a second surface opposite the surface of the imaging sensor.

17. The method of claim 1 in which attaching the two or more upconverting particles to each unit of the one or more units of the chemical component comprises
    binding two or more attachment units to each unit of the one or more units of the chemical component, each of the two or more attachment units also being bound to a corresponding upconverting particle of the two or more upconverting particles attached to the unit of the chemical component.

18. The method of claim 17 in which the two or more attachment units comprise antibodies.

19. The method of claim 17 in which the two or more attachment units comprises antigens from a pathogen, and in which the one or more units of the chemical component comprise antibodies to the pathogen.

20. The method of claim 1, in which identifying the one or more multi-particle complexes in the one or more images comprises identifying the one or more multi-particle complexes based on a proximity of the two or more upconverting particles of each multi-particle complex in a single image or based on a brightness of each multi-particle complex in the single image.

* * * * *